Sept. 10, 1974 J. B. WILLIAMS Plant Pat. 3,615
ROSE PLANT
Filed May 7, 1973
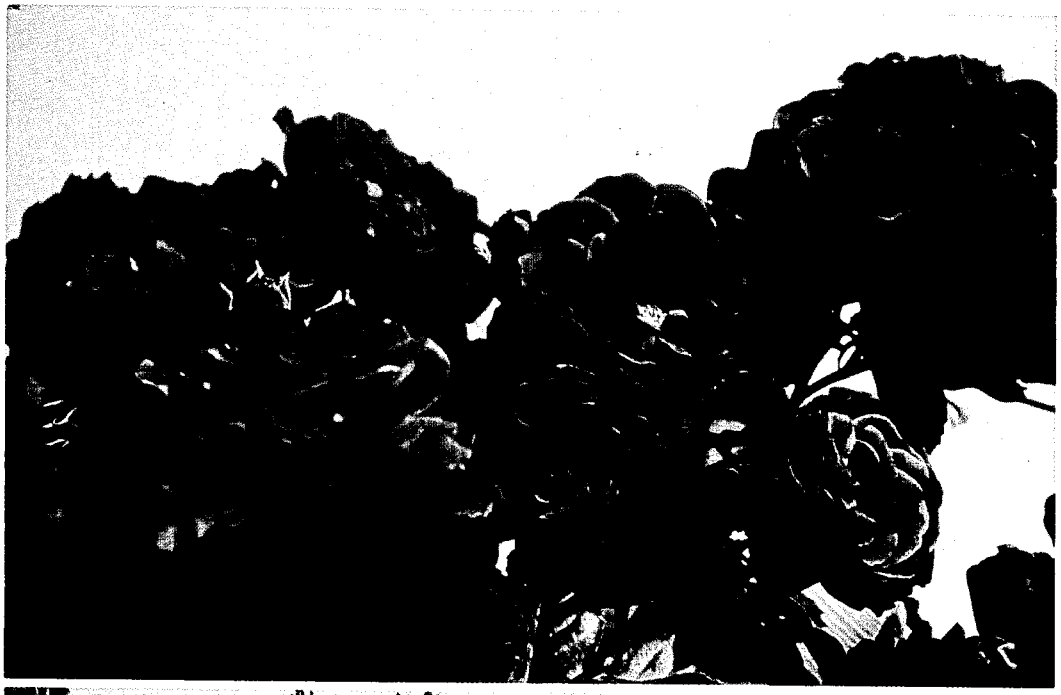
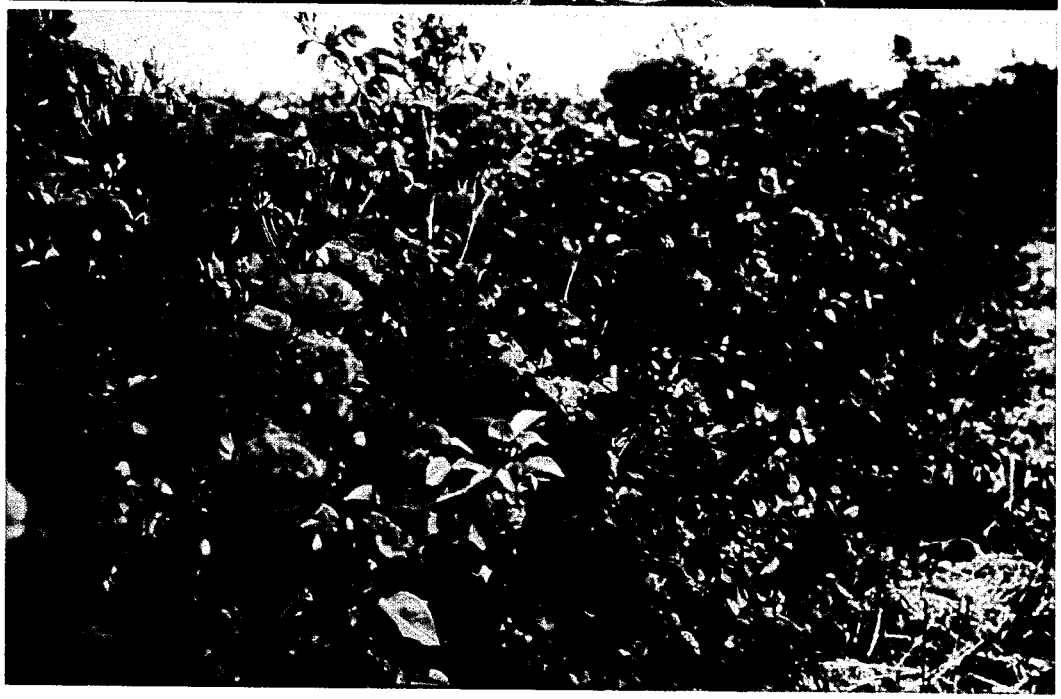

United States Patent Office

Plant Pat. 3,615
Patented Sept. 10, 1974

3,615
ROSE PLANT

J. Benjamin Williams, Silver Spring, Md., assignor to The Conard-Pyle Company, West Grove, Pa.

Filed May 7, 1973, Ser. No. 358,105
Int. Cl. A01h 5/00
U.S. Cl. Plt.—6 1 Claim

The present invention relates to a new and distinct variety of rose plant of the climbing shrub class, which was originated by me by crossing the rose variety known as "Don Juan" (Plant Pat. No. 1,864) with the rose variety known as "Blaze" (Plant Pat. No. 10).

The new variety resulted from an extensive breeding program conducted by me and having for its objective to produce improved, everblooming, red-flowered shrub type climber rose varieties, and it is one which fully achieves this objective, as evidenced by the following unique combination of characteristics which are outstanding therein and which distinguish the new variety from its parents, as well as from all other varieties of which I am aware:

(1) An everblooming, bushy, free-standing, vigorous, upright-spreading, climbing habit which can be left as a large, bushy shrub, or trained as a typical climbing plant having long arching or climbing canes up to 6 to eight feet in length on first year plants. This new variety is distinctive from both its parents in that it produces blooming lateral canes all along the new main arched canes as they are produced.

(2) The plant is ever-blooming and produces medium 2½ inch to 3½ inch flowers that last well in clusters of 5 to 7 blooms to a spray.

(3) Strong old rose fragrance;

(4) A general color tonality of the flowers corresponding to Deep Crimson, lightly overcast with Oxblood Red and the flowers are long-lasting and unfading; and (5) Good hardiness and disease resistance.

Asexual reproduction of the new variety by budding, as performed at West Grove, Pa., U.S.A., and McFarland, Calif., U.S.A., shows that the afore-mentioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature except where general color terms of ordinary dictionary significance are observed:

Type: Hardy; climbing; outdoor; seedling; for garden decoration and cutting.
Class: Climber.
Breeding: Seedling.

*Seed parent.*—"Don Juan."
*Pollen parent.*—"Blaze."

FLOWER (Observations made from specimens grown outdoors at West Grove, Pa., U.S.A., in late September.
Blooming habit: Recurrent—continuous.
Bud:
*Size.*—Medium.
*Form.*—Ovoid; is not affected by wet or hot weather.
*Color.*—When sepals first divide—Bordeaux, Plate 12. When petals begin to unfurl—Oxblood Red, Plate 1. When half-blown: inside of petals—Carmine, Plate 1, lightly overcast with Maroon, Plate 1; reverse of petals—Carmine, Plate 1, lightly overcast with Oxblood Red, Plate 1.
*Sepals.*—Slightly branched; curl back when petals begin to unfurl. Color: inside—Corydalis Green, Plate 41; outside—Light Elm Green, Plate 17, lightly overcast with Van Dyke Red, Plate 13.
*Calyx.*—Color—Biscay Green, Plate 31. Shape—pear. Size—small. Aspect—smooth. Odor when rubbed—none.
*Peduncle.*—Length — medium. Aspect — smooth. Strength—erect; heavy. Color—Brick Red, Plate 13.
*Opening.*—Opens up well; is not affected by adverse weather conditions.
Bloom:
*Size.*—Medium. Average size when fully expanded—3½ inches.
*Borne.*—Several together in large sprays.
*Form.*—High centered at first; becoming flat; petals remaining at first loosely rolled outward; becoming ruffled at maturity.
*Petalage.*—Double (full but open center). Number of petals under normal conditions—35.
*Color.*—Center of flower—Carmine, Plate 1. Outer petals—Carmine, Plate 1, lightly overcast with Oxblood Red, Plate 1. Base of petals (aiglet)—Amber Yellow, Plate 16. Inside of petals—Carmine, Plate 1, lightly overcast with Oxblood Red, Plate 1. Reverse of petals—Pomegranate Purple, Plate 12, lightly overcast with Spinel Red, Plate 26. General tonality from a distance—Carmine, Plate 1.
Petals:
*Texture.*—Thick; is not affected by wet or hot weather.
*Appearance.*—Inside—velvety. Outside—satiny.
*Form.*—Oval.
*Arrangement.* — Imbricated (regularly arranged single-like).
*Petaloids in center.*—Few; medium.
*Persistence.*—Drop off cleanly.
*Fragrance.*—Strong. Nature—old rose fragrance.
*Lasting quality.*—On the plant—very long. As cut flower—long.

GENITAL ORGANS

Stamens, anthers: Medium size; many; regularly arranged around styles.
*Color.*—Light Orange-Yellow, Plate 3.
Stamens, filaments (threads): Medium length. Color—Spinel Red, Plate 26.
Pollen: Color—Pale Yellow-Orange, Plate 3.
Styles: Bunched; uneven length; medium length; thin.
Stigmas: Color—Naples Yellow, Plate 16.
Ovaries: All enclosed in calyx.
Hips: Globular; with inconspicuous neck, smooth; walls thick and fleshy.
*Color.*—Persimmon Orange when mature.
Seeds: Not observed.

PLANT

Form: Climber.
Growth: Very vigorous; uniform branching (attains a height of from 8 to 10 feet); upright with arching habit.
Foliage: Compound of 5 to 7 leaflets.
*Size.*—Large.
*Quantity.*—Abundant.
*Color.*—New foliage: upper side—Garnet Brown, Plate 1; under side—Nopal Red, Plate 1. Old foliage: upper side—Elm Green, Plate 17; under side—Light Hellebore Green, Plate 17.
*Shape.*—Oval pointed.

*Texture.* — Upper side — leathery. Under side — smooth.

*Ribs and veins.*—Ordinary.

*Edge.*—Serrated.

*Serration.*—Both double and single; small.

*Leaf stem.*—Color—Eugenia Red, Plate 13. Under side—prickly.

*Stipules.*—Medium length; slightly bearded.

Wood:

*New wood.*—Color—Turtle Green, Plate 32, lightly overcast with Eugenia Red, Plate 13. Bark—smooth.

*Old wood.*—Color—Light Bice Green, Plate 17. Bark—smooth.

Thorns:

*Thorns.*—Quantity: on main stalks from base—ordinary; on laterals from stalk—few. Form—flat base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

1. A new and distinct variety of rose plant of the climber class, substantially as herein shown and described, characterized particularly as to novelty by its vigorous habit of growth, its good hardiness, its abundant and attractive foliage, its very good remontance, its habit of producing a cluster bloom on each new shoot, the very good form and size of its blooms, the strong and appealing fragrance of its blooms, and the general color tonality of the flowers corresponding to Carmine, lightly overcast with Oxblood Red, and the long-lasting and unfading qualities of the flower color.

No references cited.

ROBERT E. BAGWILL, Primary Examiner